US012766173B2

(12) United States Patent
Jin et al.

(10) Patent No.: US 12,766,173 B2
(45) Date of Patent: Oct. 20, 2026

(54) BACILLUS SUBTILIS ZF-1 AND APPLICATION THEREOF IN INHIBITING AFRICAN SWINE FEVER VIRUS

(71) Applicants: Huazhong Agricultural University, Wuhan (CN); Wuhan Keqian Biology Co., Ltd., Wuhan (CN)

(72) Inventors: Meilin Jin, Wuhan (CN); Changjie Lv, Wuhan (CN); Li Yang, Wuhan (CN); Chao Wu, Wuhan (CN); Chao Kang, Wuhan (CN); Zhong Zou, Wuhan (CN); Ming Zhong, Wuhan (CN); Xinxin Miao, Wuhan (CN); Junjun Tang, Wuhan (CN); Hongshuo Liu, Wuhan (CN); Xiaomei Sun, Wuhan (CN); Li Zhao, Wuhan (CN); Jingyu Yang, Wuhan (CN)

(73) Assignees: Huazhong Agricultural University, Wuhan (CN); Wuhan Keqian Biology Co., Ltd., Wuhan (CN)

( * ) Notice: Subject to any disclaimer, the term of this patent is extended or adjusted under 35 U.S.C. 154(b) by 243 days.

(21) Appl. No.: 18/607,330

(22) Filed: Mar. 15, 2024

(65) Prior Publication Data

US 2024/0261343 A1 Aug. 8, 2024

Related U.S. Application Data

(63) Continuation of application No. PCT/CN2023/090231, filed on Apr. 24, 2023.

(30) Foreign Application Priority Data

Apr. 26, 2022 (CN) ........................ 202210447852.X

(51) Int. Cl.

| | |
|---|---|
| ***A61K 35/742*** | (2015.01) |
| ***A61P 31/20*** | (2006.01) |
| ***C12N 1/205*** | (2026.01) |
| ***C12R 1/125*** | (2006.01) |

(52) U.S. Cl.

CPC ............ *A61K 35/742* (2013.01); *A61P 31/20* (2018.01); *C12N 1/205* (2021.05); *C12R 2001/125* (2021.05)

(58) Field of Classification Search

CPC ......... A61K 35/742; A61P 31/20; C12N 1/05; C12R 2001/125

See application file for complete search history.

(56) References Cited

FOREIGN PATENT DOCUMENTS

| | | | |
|---|---|---|---|
| CN | 111956702 | A | 11/2020 |
| CN | 112680388 | A | 4/2021 |
| CN | 113080309 | A | 7/2021 |
| KR | 102157964 | B1 | 9/2020 |

OTHER PUBLICATIONS

Ellis (Vaccines, W.B. Saunders Company, Chapter 29, 1988, pp. 568-574) (Year: 1988).*

Boslego et al (Vaccines and Immunotherapy, 1991, Chapter 17) (Year: 1991).*

Yu, Ning et al., "Test on using Bacillus subtilis instead of antibiotic therapy to treat piglet diarrhea," Journal of Xichang University, Natural Science Edition, vol. 23, No. 4, pp. 22-24 (Dec. 31, 2009).

Li, Xiaohui et al, "Gastric ulceration and immune suppression in weaned piglets associated with feed-borne Bacillus cereus and Aspergillus fumigatus," Toxins (Basel), vol. 12, No. 12, pp. 1-13 (Nov. 7, 2020).

* cited by examiner

*Primary Examiner* — Robert A Zeman

(74) *Attorney, Agent, or Firm* — Mei & Mark LLP; Manni Li

(57) ABSTRACT

The *Bacillus subtilis* ZF-1 and use thereof in inhibiting African swine fever virus are provided. A *Bacillus subtilis* strain (CCTCC NO: M2022185) is screened and selected from 95 self-preserved strains with an inhibiting effect on African swine fever virus. The strain has a remarkable anti-ASFV effect in vivo and in vitro through anti-infection research at a cell level and an animal body level, can reduce proliferation of the virus in a pig body and damage of ASFV infection to tissues and organs, can effectively control adverse effects of ASFV infection on the body, and can be used for preventing and controlling African swine fever epidemics.

3 Claims, 4 Drawing Sheets

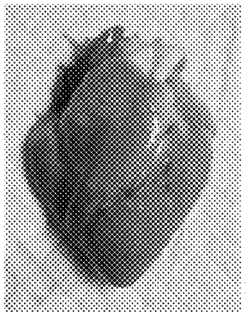
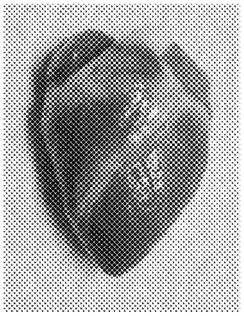
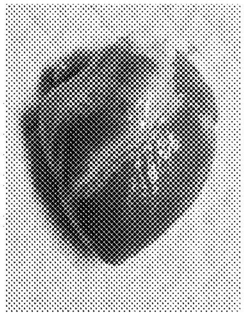
FIG. 7A FIG. 7B FIG. 7C
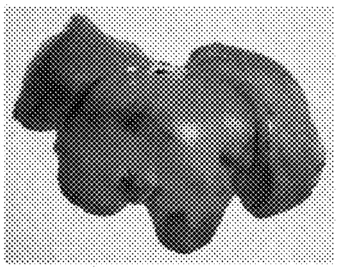
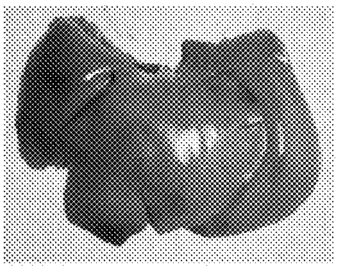
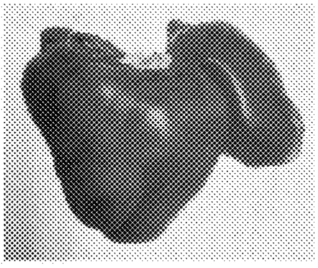
FIG. 8A FIG. 8B FIG. 8C
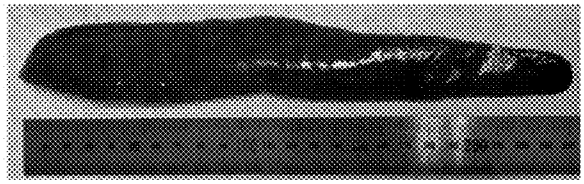
FIG. 9A
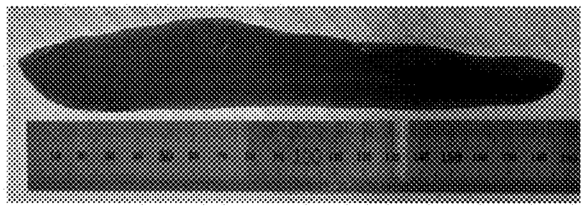
FIG. 9B
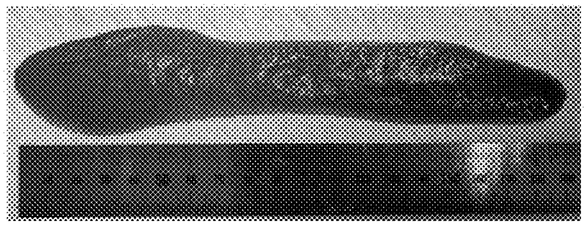
FIG. 9C

FIB. 12C

BACILLUS SUBTILIS ZF-1 AND APPLICATION THEREOF IN INHIBITING AFRICAN SWINE FEVER VIRUS

CROSS-REFERENCE TO RELATED APPLICATIONS

The subject application is a continuation of PCT/CN2023/090231 filed on Apr. 24, 2023, which in turn claims priority on Chinese Patent Application No. CN202210447852.X filed on Apr. 26, 2022 in China. The contents and subject matters of the PCT international stage application and Chinese priority application are incorporated herein by reference.

BACKGROUND OF INVENTION

Technical Field

The present invention belongs to the technical field of antiviral microecologics for livestock and poultry, and particularly relates to *Bacillus subtilis* ZF-1 and application thereof in inhibiting African swine fever virus.

Description of Related Art

African swine fever (ASF) is an acute, febrile, and highly contagious infectious disease of pigs caused by African swine fever virus infection. The main symptoms are manifested as high fever, cyanosis of the skin, and severe bleeding of lymph nodes and internal organs, and its mortality rate is as high as 100%, which is a huge harm to the pig industry. First discovered in Kenya in 1921, ASF may infect pigs of all breeds and ages, which makes it the number one threat to the global pig industry. Once pigs are infected, they can only be prevented and controlled through rapid culling. Economical, safe and effective antiviral drugs can provide effective protection, improve the effectiveness of epidemic prevention and control and reduce economic losses. Therefore, on the premise that the ASF vaccine has not yet been conquered, the development of anti-ASFV pharmaceutical formulations is also an important measure to deal with the African swine fever epidemic. Successful cases from human drug research and development show that some compound formulations have good antiviral effects and can even completely eliminate the pathogens of infection in patients. These drugs often require high research and development costs and production costs. There are many types of probiotics or microorganisms from a wide range of sources, which is a good way to develop anti-ASFV drugs. In addition, probiotics have many advantages such as no toxicity, no drug resistance, no residue, growth promotion, environmental friendliness and safety.

The prevention and control of ASF is an important problem urgently to be solved in the world's pig industry. Currently, biosecurity prevention and control are mainly concerned. Although a large number of research and development efforts on ASFV vaccines have been carried out at home and abroad and certain results have been achieved, no safe and effective commercial vaccine has been developed so far. Therefore, there is an urgent need to develop biopharmaceutical formulations that can effectively protect pigs from ASFV infection.

Although some studies have reported that *Bacillus* has the effect of resisting rotavirus, PEDV, etc., research on anti-ASFV effect has not been reported yet. Due to the particularity of ASFV, there are great difficulties in its vaccine development and drug development. Whether probiotics can resist ASFV infection has not yet been reported. Through extensive screening, the present application discovers for the first time a *Bacillus* strain that is resistant to ASFV infection, and both in vivo and in vitro research results show that it can antagonize the ASFV and reduce the proliferation of ASFV in cells. Taking functional *Bacillus* culture can resist the virulent ASFV infection. Preparing *Bacillus subtilis* into a biological formulation is low-cost, highly resistant to stress, easy to store, transport and use, affordable and effective, and provides new means and tools for ASF prevention and control.

BRIEF SUMMARY OF THE PRESENT INVENTION

The objective of the present invention is to solve the problem of difficulty in preventing and treating African swine fever virus (ASFV) infection by providing a *Bacillus subtilis* ZF-1 strain (CCTCC NO: M2022185) with an inhibiting effect on ASFV.

Another objective of the present invention is to provide a method of using *Bacillus subtilis* ZF-1 in the preparation of a pharmaceutical formulation for preventing or treating ASFV infection.

In order to achieve the above objective, the present invention adopts the following technical measures: from 95 self-preserved strains, screened out is a *Bacillus subtilis* strain (CCTCC NO: M2022185) with an inhibiting effect on African swine fever virus. The strain has been sent to the China Center for Type Culture Collection (CCTCC), having the address at Wuhan University, Luojiashan, Wuchang, Wuhan, 430072 China, for deposition on Mar. 3, 2022 under the classification name of *Bacillus subtilis* ZF-1, CCTCC NO: M2022185. The deposition has been made under the provisions of the Budapest Treaty and guarantees that the deposition is irrevocable and publicly available without restrictions or conditions after the subject application is issued as a patent.

The method of using *Bacillus subtilis* ZF-1 in the preparation of a pharmaceutical formulation for preventing or controlling ASFV infection comprises using *Bacillus subtilis* ZF-1 to prepare an inhibitor against ASFV, or a preventive pharmaceutical formulation against ASFV infection or a therapeutic pharmaceutical formulation against ASFV infection.

In the uses described above, the *Bacillus subtilis* ZF-1 comprises *Bacillus subtilis* ZF-1 cells or *Bacillus subtilis* ZF-1 fermentation supernatant.

Compared with the current technology, the present invention has the following advantages.

In the present invention, the probiotic *Bacillus subtilis* ZF-1 is used to conduct anti-infection research on ASFV at the cell level and the animal body level, and it is found that *Bacillus subtilis* ZF-1 has significant anti-ASFV effects both in vivo and in vitro. As a potential antiviral microbial formulation, *Bacillus subtilis* has the following advantages compared with vaccines and traditional antiviral chemicals. First, the *Bacillus subtilis* has a low production cost, strong stress resistance, and is easy to store, transport and use. Second, the *Bacillus subtilis* has no toxic or side effects and no residue, has anti-viral and growth-promoting effects, and is environment-friendly and safe. Third, the *Bacillus subtilis* has the advantages of convenient use, safety, no immune stress, and high economic benefits. Fourth, the *Bacillus subtilis* ZF-1 fermentation broth of the present invention, at the cell level, can reduce the infection activity of ASFV on cells, inhibit the invasion and infection of cells by ASFV, reduce the proliferation of viruses on cells, and can be used to prevent and control ASFV infection. Fifth, the *Bacillus subtilis* ZF-1 formulation in the present invention, when orally fed to test pigs, can effectively protect against morbidity and death caused by ASFV infection. The pigs in the control group die 100%. The survival rate of the pigs in the *Bacillus subtilis* formulation group reaches 100%. The *Bacillus subtilis* ZF-1 formulation significantly inhibits ASFV shedding, reduces environmental pollution, can reduce the damage of ASFV infection to tissues and organs and effectively control the adverse effects of ASFV infection on the body, and can be used for ASF prevention and control.

BRIEF DESCRIPTION OF THE SEVERAL VIEWS OF THE DRAWINGS

FIG. 1A shows the effect of fermentation broth from strain 1-30 on ASFV proliferation at the cell level, FIG. 1B shows the effect of fermentation broth from strain 31-60 on ASFV proliferation at the cell level, and FIG. 1C shows the effect of fermentation broth from strain 61-95 on ASFV proliferation at the cell level. The horizontal axis shows the number of strains screened, and the vertical axis shows the cycle threshold (Ct).

FIG. 3A shows the positive control group infected with ASFV, and FIG. 3B shows the test group orally fed with the *Bacillus subtilis* formulation. The horizontal axis shows the number of days after infection, and the vertical axis shows the body temperature (° C.).

FIG. 4A shows the positive control group infected with ASFV, and FIG. 4B shows the test group orally fed with the *Bacillus subtilis* formulation. The horizontal axis shows the number of days after infection, and the vertical axis shows the cycle threshold (Ct).

FIG. 5A shows the positive control group infected with ASFV, and FIG. 5B shows the test group orally fed with the *Bacillus subtilis* formulation. The horizontal axis shows the number of days after infection, and the vertical axis shows the cycle threshold (Ct).

FIG. 6A shows the positive control group infected with ASFV, and FIG. 6B is the test group orally fed with the *Bacillus subtilis* formulation. The horizontal axis shows the number of days after infection, and the vertical axis shows the cycle threshold (Ct).

FIGS. 7A to 7C show the effect of the *Bacillus subtilis* formulation on tissue and organ lesions in the heart of ASFV-infected pigs in the present invention, where FIG. 7A shows the control group, FIG. 7B shows the test group, and FIG. 7C shows the normal control group.

FIGS. 8A to 8C show the effect of the *Bacillus subtilis* formulation on tissue and organ lesions in the liver of ASFV-infected pigs in the present invention, where FIG. 8A shows the control group, FIG. 8B shows the test group, and FIG. 8C shows the normal control group.

FIGS. 9A to 9C show the effect of the *Bacillus subtilis* formulation on tissue and organ lesions in the spleen of ASFV-infected pigs in the present invention, where FIG. 9A shows the control group, FIG. 9B shows the test group, and FIG. 9C shows the normal control group.

FIG. 10A shows the control group, FIG. 10B shows the test group, and FIG. 10C shows the normal control group.

FIG. 11A shows the control group, FIG. 11B shows the test group, and FIG. 11C shows the normal control group.

FIGS. 12A to 12C show the effect of the *Bacillus subtilis* formulation on tissue and organ lesions in the mandibular lymph node of ASFV-infected pigs in the present invention, where FIG. 12A shows the control group, FIG. 12B shows the test group, and FIG. 12C shows the normal control group.

FIG. 13A shows the control group, FIG. 13B shows the test group, and FIG. 13C shows the normal control group.

FIG. 14A shows the control group, FIG. 14B shows the test group, and FIG. 14C shows the normal control group.

DETAILED DESCRIPTION OF THE INVENTION

Figure 1A:
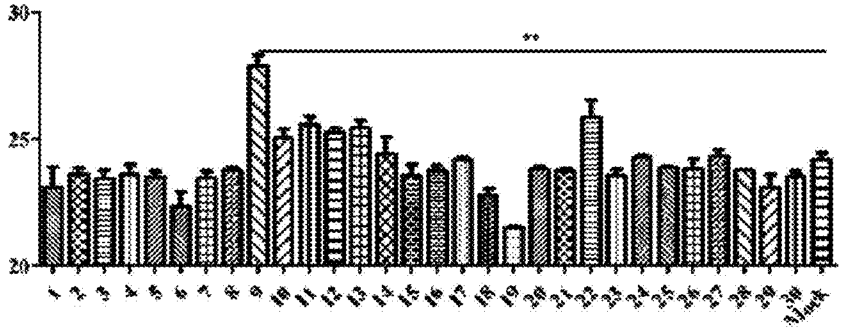
FIGS. 1A to 1C show the effects of different probiotic fermentation broths on the proliferation of ASFV at the cell level. Particularly.

To provide a better understanding of the content of the present invention, the content of the present invention will be further described below with reference to specific embodiments, but the protection content of the present invention is not limited to the following examples. The experimental methods and conditions in the following examples are conventional methods unless otherwise specified. The technical solutions of the present invention, unless otherwise specified, are conventional solutions in the field; unless otherwise specified, the reagents or materials are all sourced from commercial channels.

Example 1. Screening of Probiotic Strains Resistant to ASFV Infection

1. Isolation and Culture of Porcine Primary Alveolar Macrophages (PAM)

After the pigs were sacrificed, the chest cavity was opened, and the lungs, heart and trachea (to the larynx) were removed together. After removal, the heart was ligated to prevent blood from flowing into the lungs. Other tissues around the larynx and trachea were removed to facilitate the lung filling operation. The junction of the larynx and trachea was tied with an autoclaved rope to prevent bacteria from entering the lungs, and the lungs, heart and trachea were then placed in an autoclaved plastic bag. After the lungs were taken back, the surface and mouth of the plastic bag were disinfected with 75% alcohol, and the plastic bag was transferred to a biosafety cabinet. The lungs were taken back and placed in a sterilized tray. The outside of the lungs was rinsed with sterile PBS to wash away blood and other substances. Scissors were used to cut off excess tissues around the larynx and trachea and trim the larynx to facilitate subsequent pouring of liquid and avoid contamination of the poured liquid. Using a pipette, the culture medium supplemented with RPMI 1640 was continuously injected into the lungs through the throat, and at the same time each lung lobe was gently massaged with hands to promote the culture medium to fully enter the alveoli. When the lungs were fully filled, the liquid in the lungs was poured into a 50 mL centrifuge tube. Before pouring, the liquid on the lung surface was dried with absorbent paper to prevent blood on the lung surface from entering the medium supplemented with PAM cells during the pouring process. The cell solution was centrifuged for the first time at 500×g for 7 min at 4° C. The supernatant was discarded. 20 mL of RPMI 1640 culture medium was added to each tube to resuspend the cells. Every two tubes were combined into one tube, and the number of centrifuge tubes was reduced by half. The cell solution was centrifuged like this 3 times, and in the fourth time, the cell solution was centrifuged at 500×g for 5 min at 4° C., the supernatant was discarded, a small amount of RPMI 1640 culture medium was added to each tube to resuspend the cells, and the liquid in each centrifuge tube was sucked out into one centrifuge tube. The cell solution was filtered with a 70 μm filter to remove mucus and other substances, and then transferred to a new 50 mL centrifuge tube. 20 μl of cell solution was taken and added to the counting plate and count with an automatic cell counter. After counting, 10% FBS and RPMI 1640 culture solution were supplemented and the cells were plated in 24-welled plates with $5\times10^5$ cells/ml and then incubated in a 37° C., 5% $CO_2$ incubator.

2. Preparation of Probiotic Fermentation Broth

The plate-rejuvenated probiotics preserved in the applicant's laboratory were inoculated into 50 ml of LB liquid culture medium, incubated at 37° C. for 24 h, centrifuged at 5000 rpm for 10 min, and the supernatant was taken and stored at 4° C. for later use.

3. ASFV-Infected PAM Cells were Treated with Probiotic Fermentation Broth

The PAM cells inoculated in the 24-well plate were cultured for 24 h, the medium was then discarded, and 0.1 MOI ASFV was inoculated in the cells. The cells were incubated at 37° C. for 1 h and washed three times with PBS, and then RPMI1640 complete culture broth supplemented with fermentation supernatant of different probiotic strains was added respectively, where the concentration of probiotic fermentation broth was 1 μl/ml; and a control group without the virus treated with probiotic fermentation broth was designed. The treated 24-well plates were further cultured in a 37° C., 5% $CO_2$ incubator for 72 h.

4. Determination of ASFV Content in Cell Culture Solution

After the above treated PAM cells were cultured for 72 h, the culture was then terminated, and the cell supernatant was collected to detect the virus content. Detection was carried out according to the real-time fluorescence quantitative PCR method recommended by OIE. Primer sequences used: 5'-ctgctcatggtatcaatcttatcga-3', R:5'-gataccacaagatcrgccgt-3', probe primer was 5'-FAM-ccacgggaggaataccaacccagtg-TAMRA-3', the reaction program comprised 50° C. 2 min, 95° C. 10 min, 40 cycles comprised 95° C. 15 s, 58° C. 1 min.

Figure 1B:
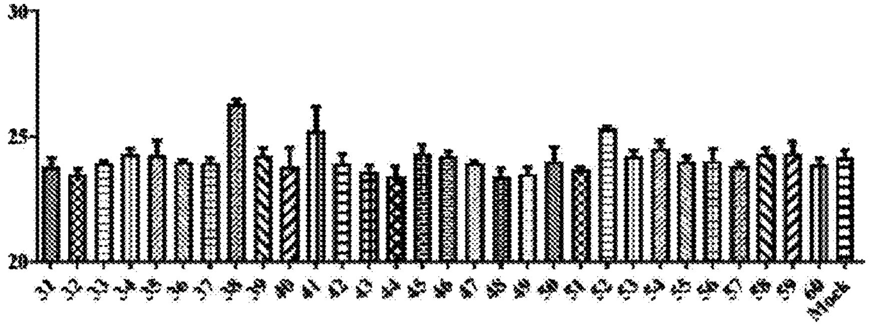
Figure 1C:
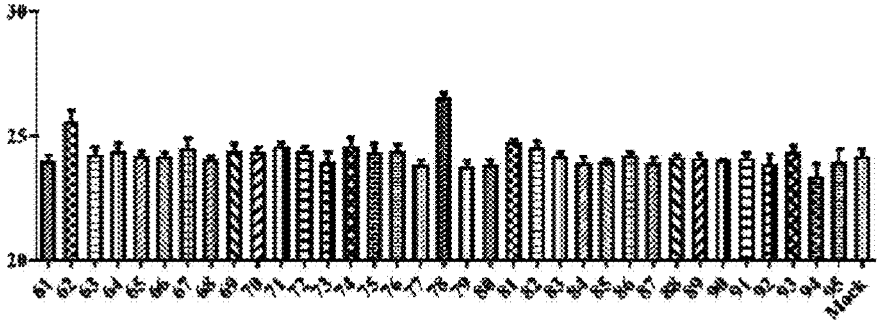

The results are shown in Table 1 and FIGS. 1A to 1C. Among the 95 probiotic strains screened, compared with the virus-positive control group, strain No. 9 was found to have a significant inhibitory effect on the proliferation of ASFV. P<0.01 and the Ct was 3.74 higher than the control group.

5. Biological Characteristics and Identification of Strain No. 9 with Anti-ASFV Activity Strain No. 9 is a Gram-positive *Bacillus* with spore formation and non-movement; the colony diameter on NA medium ranges from 2 mm to 4 mm; the colony is irregularly round. The optimal growth temperature is 30-37° C., and the optimal growth pH is 6-7. The 16SrRNA gene was PCR amplified and sequenced. The results were compared by Blast at NCBI and found that strain No. 9 has the highest similarity of 99.9% with *Bacillus subtilis*.

In the present invention, the applicant named the strain *Bacillus subtilis* ZF-1. The strain has been sent to the China Center for Type Culture Collection (CCTCC) (address: Wuhan University, Wuhan, China) for deposition on Mar. 3, 2022 under the classification name of *Bacillus subtilis* ZF-1, CCTCC NO: M2022185.

TABLE 1

Effects of probiotic fermentation broths on the proliferation of ASFV on cells

| No. | Ct |
|---|---|
| 1 | 23.07 |
| 2 | 23.59 |
| 3 | 23.41 |
| 4 | 23.59 |
| 5 | 23.49 |
| 6 | 22.27 |
| 7 | 23.44 |
| 8 | 23.73 |
| 9 | 27.89 |
| 10 | 25.02 |
| 11 | 25.55 |
| 12 | 25.25 |
| 13 | 25.44 |
| 14 | 24.38 |
| 15 | 23.55 |
| 16 | 23.72 |
| 17 | 24.15 |
| 18 | 22.79 |
| 19 | 21.47 |
| 20 | 23.77 |
| 21 | 23.72 |
| 22 | 25.84 |
| 23 | 23.54 |
| 24 | 24.24 |
| 25 | 23.83 |
| 26 | 23.78 |
| 27 | 24.28 |
| 28 | 23.73 |
| 29 | 23.07 |
| 30 | 23.51 |
| 31 | 23.79 |
| 32 | 23.49 |
| 33 | 23.94 |
| 34 | 24.29 |
| 35 | 24.25 |
| 36 | 23.99 |
| 37 | 23.97 |
| 38 | 26.31 |
| 39 | 24.23 |
| 40 | 23.79 |
| 41 | 25.22 |
| 42 | 23.92 |
| 43 | 23.61 |
| 44 | 23.4 |

TABLE 1-continued

| Effects of probiotic fermentation broths on the proliferation of ASFV on cells | |
|---|---|
| No. | Ct |
| 45 | 24.32 |
| 46 | 24.19 |
| 47 | 23.95 |
| 48 | 23.4 |
| 49 | 23.52 |
| 50 | 24.01 |
| 51 | 23.67 |
| 52 | 25.3 |
| 53 | 24.19 |
| 54 | 24.52 |
| 55 | 24.02 |
| 56 | 24.04 |
| 57 | 23.81 |
| 58 | 24.29 |
| 59 | 24.31 |
| 60 | 23.88 |
| 61 | 23.97 |
| 62 | 25.59 |
| 63 | 24.26 |
| 64 | 24.4 |
| 65 | 24.18 |
| 66 | 24.15 |
| 67 | 24.49 |
| 68 | 24.06 |
| 69 | 24.4 |
| 70 | 24.36 |
| 71 | 24.59 |
| 72 | 24.39 |
| 73 | 23.91 |
| 74 | 24.62 |
| 75 | 24.32 |
| 76 | 24.4 |
| 77 | 23.83 |
| 78 | 26.52 |
| 79 | 23.75 |
| 80 | 23.83 |
| 81 | 24.76 |
| 82 | 24.53 |
| 83 | 24.18 |
| 84 | 23.91 |
| 85 | 23.94 |
| 86 | 24.21 |
| 87 | 23.9 |
| 88 | 24.11 |
| 89 | 24.09 |
| 90 | 24.02 |
| 91 | 24.1 |
| 92 | 23.86 |
| 93 | 24.34 |
| 94 | 23.35 |
| 95 | 23.93 |
| Mock | 24.15 |

Example 2. Effects of Probiotic Formulations on ASFV Infection in Pigs

Preparation Method of Probiotic Formulation Against ASFV Infection

The frozen *Bacillus subtilis* ZF-1 was resuscitated. An appropriate amount of freeze-dried bacterial powder was picked by using an inoculating loop and inoculated on the NA solid plate medium for streak rejuvenation and cultured at 37° C. for 18-24 h. The plate-rejuvenated *Bacillus subtilis* was inoculated into the NB liquid culture medium, cultured at 37° C. and 160 rpm for 24 h. Plate counting was performed, and the concentration of the bacterial suspension was adjusted such that the number of viable bacteria reached $2\times10^8$ CFU/ml. The bacterial suspension, as an anti-ASFV probiotic formulation, was store at 4° C. for later use.

Animal Experiment Design

Ten pigs (23-day-old weaned piglets) were randomly divided into 2 groups, a test group and a control group, with 5 pigs in each group. The five pigs in the control group were numbered 51, 52, 53, 54, and 55, and the five pigs in the test group were numbered 72, 73, 74, 75, and 76. All the animals were raised in the Animal Biosafety Level 3 Laboratory (ABSL-3). The test group was orally fed with the *Bacillus subtilis* ZF-1 formulation, and each pig was orally fed with 5 ml of $2\times10^8$ CFU/ml live bacterial per day. The control group was orally fed with blank NB liquid culture medium, and each pig was orally fed with 5 ml per day. The pigs were orally fed and infected with 50 $HAD_{50}$ dose of ASFV, and probiotic formulations or blank culture medium were continuously orally fed 10 days before infection and 21 days after infection. The test groups are shown in Table 2.

TABLE 2

| Animal test groups of probiotic formulations against ASFV infection | | | |
|---|---|---|---|
| Group | −10 days | 0 day | 1-21 days. |
| Test group | $10^9$ CFU/pig/day | Orally fed with 50 $HAD_{50}$ virus | $10^9$ CFU/pig/day |
| Control group | Equal amount of culture medium/pig/day | Orally fed with 50 $HAD_{50}$ virus | Equal amount of culture medium/pig/day |

Figure 2:
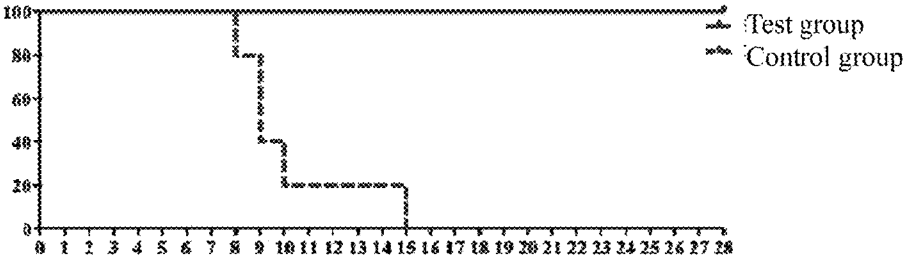
FIG. 2 shows the effect of the *Bacillus subtilis* formulation on the survival rate of ASFV infection in the present invention. The horizontal axis shows the number of days after infection, and the vertical axis shows the survival rate (%).

Effect of the *Bacillus subtilis* Formulation on Mortality of ASFV-Infected Pigs The health status of pigs was observed every day after ASFV infection. The results are shown in FIG. 2: after challenge, among pigs in the control group, one died on day 8, two died on day 9, one died on day 10, and one died on day 15, with the mortality rate of 100%, while the pigs in the *Bacillus subtilis* formulation group did not suffer from morbidity or death and were 100% alive and healthy.

Effect of the *Bacillus subtilis* Formulation on Body Temperature of ASFV-Infected Pigs After ASFV infection, the body temperature of pigs was measured every day for a total of 28 days. All pigs in the control group died on day 15. The pigs in the control group were dissected immediately after death to observe the visceral lesions. The pigs in the test group were all dissected at the end of the experiment on day 28 to observe internal organs.

Figure 3A:
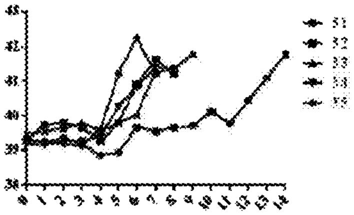
FIGS. 3A and 3B show the effect of the *Bacillus subtilis* formulation on the body temperature of ASFV-infected pigs in the present invention, where
Figure 3B:
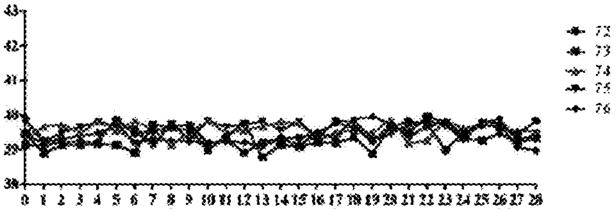

The results are shown in Table 3 and FIGS. 3A and 3B. The body temperature of pigs No. 55 and 54 exceeded 40° C. on day 5 after infection until death on day 8 and day 9. The body temperature of pigs No. 52 and 53 exceeded 40° C. on day 6 after infection until death on day 9 and day 10. The body temperature of pigs No. 51 exceeded 40° C. on day 10 until death on day 15. The body temperature of the pigs in the *Bacillus subtilis* formulation group was stable below 40° C.

TABLE 3

Effect of the *Bacillus subtilis* formulation on body temperature of ASFV-infected pigs

| Days after infection | Body temperature of control pig (° C.) | | | | | Body temperature of test pig (° C.) | | | | |
|---|---|---|---|---|---|---|---|---|---|---|
| | 51# | 52# | 53# | 54# | 55# | 72# | 73# | 74# | 75# | 76# |
| 0 | 39.22 | 39.25 | 39.46 | 39.16 | 39.27 | 39.12 | 39.45 | 39.28 | 39.83 | 39.39 |
| 1 | 39.21 | 39.72 | 39.53 | 39.14 | 39.24 | 39.12 | 38.89 | 39.67 | 39.24 | 39.21 |
| 2 | 39.34 | 39.79 | 39.61 | 39.26 | 39.17 | 39.21 | 39.13 | 39.72 | 39.47 | 39.3 |
| 3 | 39.15 | 39.64 | 39.78 | 39.24 | 39.12 | 39.22 | 39.13 | 39.45 | 39.66 | 39.4 |
| 4 | 38.84 | 39.25 | 39.52 | 39.41 | 39.62 | 39.21 | 39.16 | 39.82 | 39.81 | 39.45 |
| 5 | 38.92 | 39.78 | 39.79 | 40.27 | 41.21 | 39.89 | 39.13 | 39.54 | 39.67 | 39.671 |
| 6 | 39.64 | 40.89 | 40.03 | 40.82 | 42.24 | 39.45 | 38.91 | 39.83 | 39.58 | 39.2 |
| 7 | 39.52 | 41.63 | 41.26 | 41.39 | 41.22 | 39.52 | 39.73 | 39.56 | 39.12 | 39.3 |
| 8 | 39.63 | 41.20 | 41.33 | 41.35 | Dead | 39.66 | 39.62 | 39.14 | 39.74 | 39.24 |
| 9 | 39.69 | Dead | 41.78 | Dead | | 39.72 | 39.54 | 39.47 | 39.26 | 39.23 |
| 10 | 40.13 | | Dead | | | 39.17 | 39.00 | 39.83 | 39.84 | 39.19 |
| 11 | 39.77 | | | | | 39.27 | 39.34 | 39.46 | 39.65 | 39.24 |
| 12 | 40.44 | | | | | 38.91 | 39.76 | 39.55 | 39.72 | 39.2 |
| 13 | 41.09 | | | | | 39.21 | 38.79 | 39.67 | 39.82 | 39.09 |
| 14 | 41.76 | | | | | 39.32 | 39.14 | 39.81 | 39.56 | 39.32 |
| 15 | Dead | | | | | 39.34 | 39.07 | 39.75 | 39.81 | 39.12 |
| 16 | | | | | | 39.45 | 39.21 | 39.26 | 39.32 | 39.45 |
| 17 | | | | | | 39.78 | 39.18 | 39.49 | 39.84 | 39.32 |
| 18 | | | | | | 39.61 | 39.35 | 39.51 | 39.81 | 39.89 |
| 19 | | | | | | 39.24 | 38.87 | 39.46 | 39.26 | 39.97 |
| 20 | | | | | | 39.64 | 39.68 | 39.88 | 39.45 | 39.74 |
| 21 | | | | | | 39.83 | 39.49 | 39.17 | 39.71 | 39.36 |
| 22 | | | | | | 39.75 | 39.97 | 39.26 | 39.84 | 39.66 |
| 23 | | | | | | 38.99 | 39.78 | 39.84 | 39.69 | 39.82 |
| 24 | | | | | | 39.46 | 39.32 | 39.61 | 39.29 | 39.43 |
| 25 | | | | | | 39.71 | 39.26 | 39.72 | 39.78 | 39.81 |
| 26 | | | | | | 39.65 | 39.47 | 39.63 | 39.89 | 39.76 |
| 27 | | | | | | 39.41 | 39.21 | 39.52 | 39.26 | 39.06 |
| 28 | | | | | | 39.84 | 39.32 | 39.49 | 39.43 | 38.97 |

Figure 4A:
FIGS. 4A and 4B show the effect of the *Bacillus subtilis* formulation on the virus content of anal swabs from ASFV-infected pigs in the present invention, where
Figure 4B:
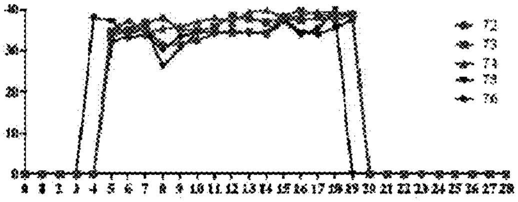

Effect of the *Bacillus subtilis* Formulation on the Virus Content of Anal Swabs from ASFV-Infected Pigs After ASFV infection, anal swabs were collected from pigs every day for a total of 28 days, and the ASFV content in the anal swabs was detected using the real-time fluorescence quantitative PCR recommended by OIE. The results are shown in table 4 and FIGS. 4A and 4B.

The pigs in the control group began virus shedding in the intestines on day 3 after infection, and the Ct of the anal swab from pig No. 54 reached the level of 17.54 at least on day 6 after infection in terms of virus shedding. The anal swabs collected from pigs in the control group in several days before death all had high Ct in terms of virus shedding.

The pigs in the *Bacillus subtilis* formulation group began virus shedding on day 5, and the virus content in the anal swabs was significantly lower than that in the control group. The Ct of pig No. 75 on day 8 was 26.24, but after day 9, the Ct was greater than 30 until no Ct was detected on day 19. In FIG. 4, no Ct is represented by 0. The results show that the use of *Bacillus subtilis* ZF-1 formulation can reduce the content of ASFV in anal swabs of infected pigs and the virus shedding in the intestines and feces of infected pigs.

TABLE 4

Effect of the *Bacillus subtilis* formulation on the virus shedding (Ct) of anal swabs from ASFV-infected pigs

| Days after infection | Ct of control pig | | | | | Ct of test pig | | | | |
|---|---|---|---|---|---|---|---|---|---|---|
| | 51# | 52# | 53# | 54# | 55# | 72# | 73# | 74# | 75# | 76# |
| 0 | No Ct | No Ct | No Ct | No Ct | No Ct | No Ct | No Ct | No Ct | No Ct | No Ct |
| 1 | No Ct | No Ct | No Ct | No Ct | No Ct | No Ct | No Ct | No Ct | No Ct | No Ct |
| 2 | No Ct | No Ct | No Ct | No Ct | No Ct | No Ct | No Ct | No Ct | No Ct | No Ct |
| 3 | No Ct | No Ct | No Ct | 38.79 | 37.45 | No Ct | No Ct | No Ct | No Ct | No Ct |
| 4 | 36.73 | 35.42 | 35.84 | 37.87 | 33.94 | No Ct | No Ct | No Ct | No Ct | 38.13 |
| 5 | 30.69 | 29.87 | 30.12 | 27.44 | 28.30 | 33.83 | 34.82 | 34.96 | 32.05 | 37.34 |
| 6 | 33.23 | 26.73 | 29.76 | 17.54 | 20.96 | 34.32 | 35.16 | 37.24 | 33.75 | 33.29 |
| 7 | 32.09 | 122.96 | 24.38 | 24.82 | 25.42 | 35.78 | 36.72 | 34.27 | 35.81 | 33.83 |
| 8 | 34.84 | 22.73 | 23.12 | 22.97 | Dead | 31.46 | 37.83 | 35.39 | 26.24 | 30.43 |
| 9 | 30.83 | Dead | 23.67 | Dead | | 31.73 | 35.26 | 35.78 | 30.78 | 33.44 |
| 10 | 32.05 | | Dead | | | 32.53 | 34.89 | 36.93 | 34.45 | 34.60 |
| 11 | 30.83 | | | | | 34.33 | 35.74 | 37.92 | 34.36 | 34.33 |
| 12 | 29.44 | | | | | 34.23 | 38.41 | 36.85 | 34.15 | 35.03 |
| 13 | 28.84 | | | | | 34.71 | 37.69 | 39.46 | 34.46 | 34.29 |
| 14 | 26.71 | | | | | 34.07 | 36.83 | 39.83 | 34.34 | 34.09 |
| 15 | Dead | | | | | 38.25 | 37.79 | 37.94 | 38.09 | 37.16 |

TABLE 4-continued

Effect of the *Bacillus subtilis* formulation on the virus shedding (Ct) of anal swabs from ASFV-infected pigs

| Days after infection | Ct of control pig 51# | 52# | 53# | 54# | 55# | Ct of test pig 72# | 73# | 74# | 75# | 76# |
|---|---|---|---|---|---|---|---|---|---|---|
| 16 | | | | | | 39.84 | 37.24 | 38.52 | 34.29 | 34.12 |
| 17 | | | | | | 38.53 | 38.15 | 39.41 | 35.29 | 34.06 |
| 18 | | | | | | 38.71 | 37.39 | 39.26 | 39.87 | 35.72 |
| 19 | | | | | | 38.64 | 38.97 | 38.96 | No Ct | 37.32 |
| 20 | | | | | | No Ct | No Ct | No Ct | No Ct | No Ct |
| 21 | | | | | | No Ct | No Ct | No Ct | No Ct | No Ct |
| 22 | | | | | | No Ct | No Ct | No Ct | No Ct | No Ct |
| 23 | | | | | | No Ct | No Ct | No Ct | No Ct | No Ct |
| 24 | | | | | | No Ct | No Ct | No Ct | No Ct | No Ct |
| 25 | | | | | | No Ct | No Ct | No Ct | No Ct | No Ct |
| 26 | | | | | | No Ct | No Ct | No Ct | No Ct | No Ct |
| 27 | | | | | | No Ct | No Ct | No Ct | No Ct | No Ct |
| 28 | | | | | | No Ct | No Ct | No Ct | No Ct | No Ct |

Effect of the *Bacillus subtilis* Formulation on the Virus Content of Throat Swabs from ASFV-Infected Pigs After ASFV infection, throat swabs were collected from pigs every day for a total of 28 days, and the ASFV content in the throat swabs was detected using the real-time fluorescence quantitative PCR recommended by OIE.

Figure 5A:
FIGS. 5A and 5B show the effect of the *Bacillus subtilis* formulation on the virus content of throat swabs from ASFV-infected pigs in the present invention, where
Figure 5B:
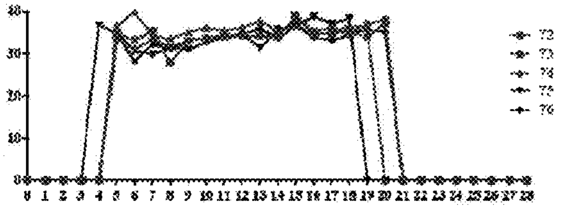

The results are shown in Table 5 and FIG. 5. The pigs in the control group began virus shedding in the upper respiratory tract on day 3 after infection, and the Ct of the throat swab from pig No. 54 reached the level of 21.67 at least on day 8 after infection in terms of virus shedding. The throat swabs collected from pigs in the control group in several days before death all have high virus shedding level. The pigs in the *Bacillus subtilis* formulation group began to virus shedding on day 4, and the virus content in the throat swabs was significantly lower than that in the control group. The Ct of pig No. 73 on day 8 was 27.92, but after day 9, the Ct was greater than 30 or no Ct was detected. There was no Ct detected in the throat swabs from pigs in the test group 21 days after infection. No Ct is represented by 0 in FIGS. 5A and 5B. The results show that the use of *Bacillus subtilis* ZF-1 formulation can reduce the content of ASFV in throat swabs from infected pigs and the virus shedding in the upper respiratory tract of infected pigs.

TABLE 5

Effect of the *Bacillus subtilis* formulation on the virus shedding (Ct) of throat swabs from ASFV-infected pigs

| Days after infection | Ct of control pig 51# | 52# | 53# | 54# | 55# | Ct of test pig 72# | 73# | 74# | 75# | 76# |
|---|---|---|---|---|---|---|---|---|---|---|
| 0 | No Ct | No Ct | No Ct | No Ct | No Ct | No Ct | No Ct | No Ct | No Ct | No Ct |
| 1 | No Ct | No Ct | No Ct | No Ct | No Ct | No Ct | No Ct | No Ct | No Ct | No Ct |
| 2 | No Ct | No Ct | No Ct | No Ct | No Ct | No Ct | No Ct | No Ct | No Ct | No Ct |
| 3 | 39.48 | 3:5.19 | No Ct | 37.52 | No Ct | No Ct | No Ct | No Ct | No Ct | No Ct |
| 4 | 37.31 | 3:4.86 | No Ct | 38.91 | 36.28 | No Ct | No Ct | No Ct | 36.84 | No Ct |
| 5 | 38.46 | 30.43 | 33.92 | 33.21 | 33.76 | 33.41 | 34.85 | 36.78 | 34.93 | 34.82 |
| 6 | 31.38 | 27.93 | 29.87 | 26.45 | 29.34 | 31.10 | 33.36 | 39.84 | 30.47 | 28.26 |
| 7 | 33.92 | 26.54 | 26.71 | 24.59 | 26.89 | 33.39 | 35.53 | 34.29 | 29.83 | 32.31 |
| 8 | 34.82 | 24.12 | 25.13 | 21.67 | Dead | 31.55 | 27.92 | 33.72 | 31.48 | 31.1 |
| 9 | 31.43 | Dead | 24.38 | Dead | | 33.15 | 33.21 | 35.19 | 31.09 | 33.21 |
| 10 | 28.98 | | Dead | | | 33.88 | 33.66 | 36.23 | 32.72 | 33.99 |
| 11 | 28.83 | | | | | 34.45 | 34.19 | 35.47 | 33.97 | 33.87 |
| 12 | 27.83 | | | | | 34.36 | 34.36 | 36.27 | 34.92 | 34.67 |
| 13 | 25.65 | | | | | 34.26 | 34.34 | 37.84 | 31.36 | 35.97 |
| 14 | 24.92 | | | | | 34.58 | 34.06 | 35.26 | 35.84 | 33.62 |
| 15 | Dead | | | | | 38.16 | 39.24 | 36.72 | 36.79 | 36.70 |
| 16 | | | | | | 35.43 | 35.01 | 34.92 | 38.90 | 33.97 |
| 17 | | | | | | 36.17 | 35.01 | 34.88 | 37.21 | 33.14 |
| 18 | | | | | | 34.89 | 35.21 | 36.75 | 38.44 | 34.73 |
| 19 | | | | | | 37.18 | 34.07 | 36.29 | No Ct | 35.86 |
| 20 | | | | | | 38.07 | 37.23 | No Ct | No Ct | 35.26 |
| 21 | | | | | | No Ct | No Ct | No Ct | No Ct | No Ct |
| 22 | | | | | | No Ct | No Ct | No Ct | No Ct | No Ct |
| 23 | | | | | | No Ct | No Ct | No Ct | No Ct | No Ct |
| 24 | | | | | | No Ct | No Ct | No Ct | No Ct | No Ct |
| 25 | | | | | | No Ct | No Ct | No Ct | No Ct | No Ct |
| 26 | | | | | | No Ct | No Ct | No Ct | No Ct | No Ct |
| 27 | | | | | | No Ct | No Ct | No Ct | No Ct | No Ct |
| 28 | | | | | | No Ct | No Ct | No Ct | No Ct | No Ct |

Effect of the *Bacillus subtilis* Formulation on the Virus Content of Nose Swabs from ASFV-Infected Pigs After ASFV infection, nose swabs were collected from pigs every day for a total of 28 days, and the ASFV content in the nose swabs was detected using the real-time fluorescence quantitative PCR recommended by OIE.

Figure 6A:
FIGS. 6A and 6B show the effect of the *Bacillus subtilis* formulation on the virus content of nose swabs from ASFV-infected pigs in the present invention, where
Figure 6B:
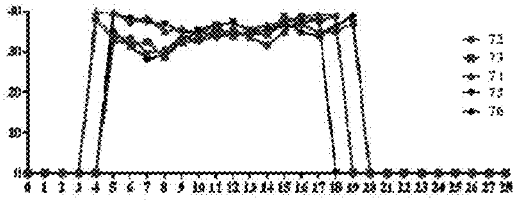
Figure 10A:
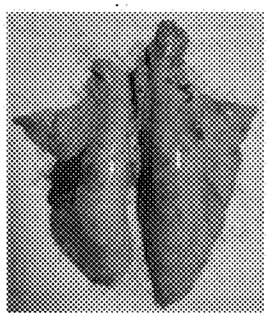
FIGS. 10A to 10C show the effect of the *Bacillus subtilis* formulation on tissue and organ lesions in the lung of ASFV-infected pigs in the present invention, where
Figure 10B:
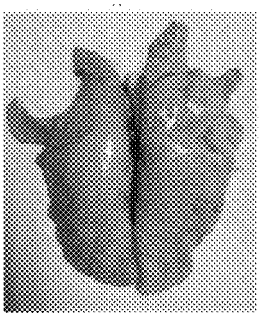
Figure 10C:
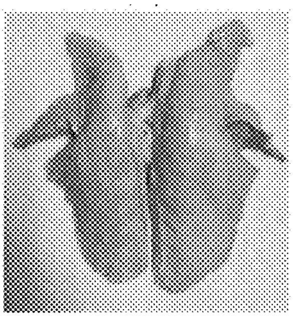
Figure 11A:
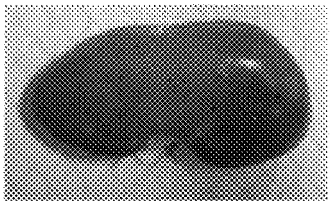
FIGS. 11A to 11C show the effect of the *Bacillus subtilis* formulation on tissue and organ lesions in the kidney of ASFV-infected pigs in the present invention, where
Figure 11B:
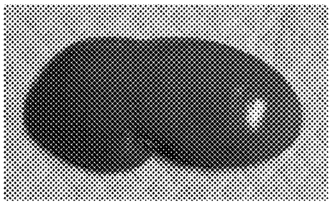
Figure 11C:
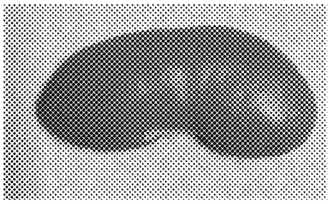
Figure 12A:
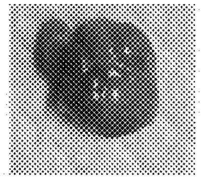
Figure 12B:
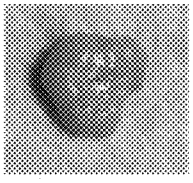
Figure 13A:
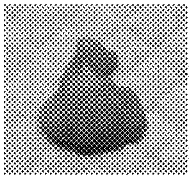
FIGS. 13A to 13C show the effect of the *Bacillus subtilis* formulation on tissue and organ lesions in the inguinal lymph node of ASFV-infected pigs in the present invention, where
Figure 13A:
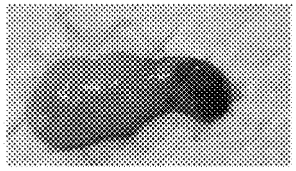
Figure 13B:
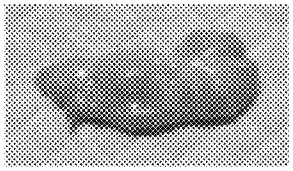
Figure 13C:
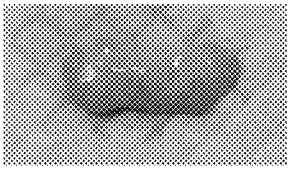
Figure 14A:
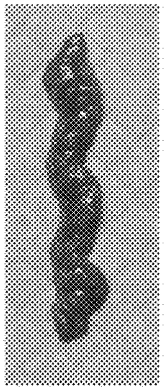
FIGS. 14A to 14C show the effect of the *Bacillus subtilis* formulation on tissue and organ lesions in the mesenteric lymph node of ASFV-infected pigs in the present invention, where
Figure 14B:
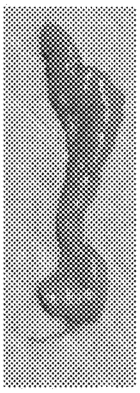
Figure 14C:
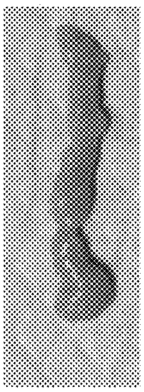

The results are shown in Table 6 and FIGS. 6A and 6B. The pigs in the control group began virus shedding in the nasal cavity on day 3 after infection, and the Ct of the nose swab from pig No. 54 reached the level of 18.27 at least on day 7 after infection in terms of virus shedding. The nose swabs collected from pigs in the control group in several days before death all have high virus shedding level. The pigs in the *Bacillus subtilis* formulation group began to virus shedding on day 4, and the virus content in the throat swabs was significantly lower than that in the control group. The Ct of pig No. 76 on day 7 was 28.29, after that, the Ct was greater than 30 or no Ct was detected. There was no Ct detected in the throat swabs from pigs in the test group 20 days after infection. No Ct is represented by 0 in FIG. 6. The results show that the use of *Bacillus subtilis* ZF-1 formulation can reduce the content of ASFV in nose swabs from infected pigs and the virus shedding in the nasal cavity of infected pigs.

heart, liver, spleen, lung, kidney, mandibular lymph node, mesenteric lymph node, and inguinal lymph node. As shown in FIGS. 7A to 7C, the hearts of pigs infected with ASFV in the control group had obvious bleeding, but no abnormality was found in the hearts of pigs in the test group and the normal negative control group; FIGS. 8A to 8C show that the livers of pigs infected with ASFV in the control group had serious bleeding, but very slight bleeding was found in the livers of the pigs in the test group that were orally fed with the *Bacillus subtilis* formulation; FIGS. 9A to 9C show that splenomegaly is also a typical symptom of ASFV infection, the spleens of pigs infected with ASFV in the control group showed bleeding and enlargement and were 240 mm long, but the spleens of pigs in the test group and the uninfected normal control group did not show bleeding and enlargement and were basically the same in length of 190 mm; FIGS. 10A to 10C show that the lungs of pigs infected with ASFV in the control group showed pneumonary carnification, but no abnormality was found in the lungs of pigs in the test group and the normal control group; FIGS. 11A to 11C show that the kidneys of pigs infected with ASFV in the control group showed needle-like bleeding spots, but no abnormality was found in the kidneys of pigs in the test group and the normal control group; FIGS. 12A to 12C, 13A to 13C, an 14A to 14C respectively show that the mandibular lymph nodes, mesenteric lymph nodes, and inguinal lymph nodes of pigs infected with ASFV in the control group all showed congestion, but no abnormality was found in the three lymph nodes of the pigs in the test group and the normal control group. In summary, oral administration of the *Bacillus subtilis* formulation can significantly reduce the degree of tissue and organ damage caused by ASFV.

TABLE 6

Effect of the *Bacillus subtilis* formulation on the virus shedding (Ct) of nose swabs from ASFV-infected pigs

| Days after | Ct of control pig | | | | | Ct of test pig | | | | |
|---|---|---|---|---|---|---|---|---|---|---|
| infection | 51# | 52# | 53# | 54# | 55# | 72# | 73# | 74# | 75# | 76# |
| 0 | No Ct | No Ct | No Ct | No Ct | No Ct | No Ct | No Ct | No Ct | No Ct | No Ct |
| 1 | No Ct | No Ct | No Ct | No Ct | No Ct | No Ct | No Ct | No Ct | No Ct | No Ct |
| 2 | No Ct | No Ct | No Ct | No Ct | No Ct | No Ct | No Ct | No Ct | No Ct | No Ct |
| 3 | 39.26 | 39.82 | 37.21 | 37.65 | No Ct | No Ct | No Ct | No Ct | No Ct | No Ct |
| 4 | 39.30 | 38.49 | 34.27 | 35.20 | 38.66 | 37.98 | No Ct | 39.87 | No Ct | No Ct |
| 5 | 33.47 | 31.42 | 32.65 | 33.90 | 34.12 | 33.63 | 32.93 | 39.76 | 39.13 | 35.14 |
| 6 | 30.89 | 27.39 | 30.18 | 25.73 | 25.33 | 33.53 | 31.79 | 37.26 | 38.26 | 31.57 |
| 7 | 33.12 | 27.84 | 26.37 | 18.27 | 24.41 | 29.78 | 32.49 | 38.47 | 37.43 | 28.29 |
| 8 | 33.04 | 22.16 | 24.85 | 19.72 | Dead | 30.42 | 28.84 | 35.14 | 36.89 | 29.26 |
| 9 | 30.43 | Dead | 23.64 | Dead | | 33.61 | 32.28 | 35.69 | 34.82 | 32.93 |
| 10 | 33.06 | | Dead | | | 32.81 | 32.92 | 34.38 | 35.17 | 35.32 |
| 11 | 25.52 | | | | | 33.99 | 35.59 | 36.73 | 36.72 | 33.64 |
| 12 | 26.32 | | | | | 35.38 | 34.56 | 33.92 | 37.26 | 34.44 |
| 13 | 25.39 | | | | | 33.54 | 34.95 | 35.17 | 35.17 | 34.49 |
| 14 | 24.43 | | | | | 31.67 | 34.34 | 36.85 | 35.34 | 34.36 |
| 15 | Dead | | | | | 34.85 | 38.70 | 37.26 | 36.27 | 37.35 |
| 16 | | | | | | 38.76 | 36.73 | 38.64 | 37.15 | 34.88 |
| 17 | | | | | | 37.64 | 34.78 | 39.15 | 38.23 | 33.97 |
| 18 | | | | | | 38.73 | 35.08 | 38.94 | No Ct | 36.65 |
| 19 | | | | | | No Ct | 37.08 | No Ct | No Ct | 38.82 |
| 20 | | | | | | No Ct | No Ct | No Ct | No Ct | No Ct |
| 21 | | | | | | No Ct | No Ct | No Ct | No Ct | No Ct |
| 22 | | | | | | No Ct | No Ct | No Ct | No Ct | No Ct |
| 23 | | | | | | No Ct | No Ct | No Ct | No Ct | No Ct |
| 24 | | | | | | No Ct | No Ct | No Ct | No Ct | No Ct |
| 25 | | | | | | No Ct | No Ct | No Ct | No Ct | No Ct |
| 26 | | | | | | No Ct | No Ct | No Ct | No Ct | No Ct |
| 27 | | | | | | No Ct | No Ct | No Ct | No Ct | No Ct |
| 28 | | | | | | No Ct | No Ct | No Ct | No Ct | No Ct |

8. Effect of the *Bacillus subtilis* Formulation on Tissue Lesions in ASFV-Infected Pigs The pigs in the control group were dissected immediately after death due to infection with ASFV. The pigs in the test group that were orally fed with the *Bacillus subtilis* formulation were observed to be dissected on day 28 after infection, and the normal pigs of the same age that were not infected with ASFV were dissected at the same time. The following tissue samples were collected for observation:

We claim:

1. A method for treating an African swine fever (ASFV) infected subject comprising administering a biological formulation to an ASFV infected subject, wherein the biological formulation comprises the isolated *Bacillus subtilis* strain ZF-1 deposited with the CCTCC under the accession number CCTCC NO: M2022185.

2. The method for treating an ASFV infected subject according to claim 1, wherein the ASFV infected subject is orally administered with the biological formulation.

3. The method for treating an ASFV infected subject according to claim 2, wherein a daily dosage for oral administration is 5 ml at a concentration of the isolated *Bacillus subtilis* strain ZF-1 in the biological formulation at $2\times10^8$ CFU/ml.

* * * * *